United States Patent
Chavan et al.

(10) Patent No.: US 11,246,513 B2
(45) Date of Patent: Feb. 15, 2022

(54) DATA MANAGEMENT SYSTEM COMMUNICATIONS WITH A DISPLAY DEVICE IN AN ANALYTE MONITORING SYSTEM

(71) Applicant: Senseonics, Incorporated, Germantown, MD (US)

(72) Inventors: Abhi Chavan, Germantown, MD (US); Barkha Raisoni, Germantown, MD (US); Suresh Addaguduru, Germantown, MD (US)

(73) Assignee: Senseonics, Incorporated, Germantown, MD (US)

(*) Notice: Subject to any disclaimer, the term of this patent is extended or adjusted under 35 U.S.C. 154(b) by 446 days.

(21) Appl. No.: 16/271,010

(22) Filed: Feb. 8, 2019

(65) Prior Publication Data

US 2019/0239784 A1 Aug. 8, 2019

Related U.S. Application Data

(60) Provisional application No. 62/627,904, filed on Feb. 8, 2018.

(51) Int. Cl.
*A61B 5/145* (2006.01)
*A61B 5/00* (2006.01)
(Continued)

(52) U.S. Cl.
CPC ........ *A61B 5/14546* (2013.01); *A61B 5/0031* (2013.01); *A61B 5/14503* (2013.01);
(Continued)

(58) Field of Classification Search
CPC ............ A61B 5/14532; A61B 5/14546; A61B 5/0031; A61B 5/7425; A61B 5/746; A61B 5/14503; A61B 2560/0214
See application file for complete search history.

(56) References Cited

U.S. PATENT DOCUMENTS 9,962,081 B2 5/2018 Mensinger et al.
2001/0023419 A1 9/2001 Lapointe et al.
(Continued)

FOREIGN PATENT DOCUMENTS

EP 2183671 B1 8/2018

*Primary Examiner* — Chu Chuan Liu
(74) *Attorney, Agent, or Firm* — Rothwell, Figg, Ernst & Manbeck, P.C.

(57) ABSTRACT

An analyte monitoring system may include one or more of an analyte sensor, a transceiver, a display device, and a management system. The transceiver may be configured to receive sensor data from the analyte sensor and calculate analyte monitoring information. The display device may be configured to receive the analyte monitoring information from the transceiver. The management system may be configured to receive analyte monitoring information from the display device. The management system may be configured to use the analyte monitoring information to produce a comparison result. The management system may be configured to, based on the comparison result, transmit to the display device management information associated with the received analyte monitoring information. Producing the comparison result may include comparing one or more performance diagnostics with one or more performance indicators. Producing the comparison result may include comparing compliance information with usage protocol information.

31 Claims, 7 Drawing Sheets

(51) Int. Cl.
  *H04W 4/80* (2018.01)
  *H04W 4/38* (2018.01)
  *G16H 10/60* (2018.01)
  *H04M 1/72412* (2021.01)
  *H04L 29/08* (2006.01)

(52) U.S. Cl.
  CPC ............ *A61B 5/746* (2013.01); *A61B 5/7425* (2013.01); *G16H 10/60* (2018.01); *H04M 1/72412* (2021.01); *H04W 4/38* (2018.02); *H04W 4/80* (2018.02); *A61B 2560/0214* (2013.01); *H04L 67/12* (2013.01)

(56) References Cited

U.S. PATENT DOCUMENTS

| | | |
|---|---|---|
| 2014/0184422 A1 | 7/2014 | Mesinger et al. |
| 2016/0345874 A1 | 12/2016 | Raisoni et al. |
| 2017/0100035 A1 | 4/2017 | Heikenfeld |
| 2018/0027104 A1* | 1/2018 | Mandapaka ............ A61B 5/742 455/41.3 |
| 2018/0103879 A1 | 4/2018 | Masciotti et al. |

\* cited by examiner

DATA MANAGEMENT SYSTEM COMMUNICATIONS WITH A DISPLAY DEVICE IN AN ANALYTE MONITORING SYSTEM

CROSS-REFERENCE TO RELATED APPLICATION

The present application claims the benefit of priority to U.S. Provisional Application Ser. No. 62/627,904, filed on Feb. 8, 2018, which is incorporated herein by reference in its entirety.

BACKGROUND

Field of Invention

Aspects of the present invention may relate to methods and systems for data management communications with a display device in an analyte monitoring system. More specifically, some aspects of the present invention may relate to a management system that manages communications with a display device in an analyte monitoring system.

Discussion of the Background

The prevalence of diabetes mellitus continues to increase in industrialized countries, and projections suggest that this figure will rise to 4.4% of the global population (366 million individuals) by the year 2030. Glycemic control is a key determinant of long-term outcomes in patients with diabetes, and poor glycemic control is associated with retinopathy, nephropathy and an increased risk of myocardial infarction, cerebrovascular accident, and peripheral vascular disease requiring limb amputation. Despite the development of new insulins and other classes of antidiabetic therapy, roughly half of all patients with diabetes do not achieve recommended target hemoglobin A1c (HbA1c) levels <7.0%.

Frequent self-monitoring of blood glucose (SMBG) is necessary to achieve tight glycemic control in patients with diabetes mellitus, particularly for those requiring insulin therapy. However, current blood (finger-stick) glucose tests are burdensome, and, even in structured clinical studies, patient adherence to the recommended frequency of SMBG decreases substantially over time. Moreover, finger-stick measurements only provide information about a single point in time and do not yield information regarding intraday fluctuations in blood glucose levels that may more closely correlate with some clinical outcomes.

Continuous glucose monitors (CGMs) have been developed in an effort to overcome the limitations of finger-stick SMBG and thereby help improve patient outcomes. These systems enable increased frequency of glucose measurements and a better characterization of dynamic glucose fluctuations, including episodes of unrealized hypoglycemia. Furthermore, integration of CGMs with automated insulin pumps allows for establishment of a closed-loop "artificial pancreas" system to more closely approximate physiologic insulin delivery and to improve adherence.

Monitoring real-time analyte measurements from a living body via wireless analyte monitoring sensor(s) may provide numerous health and research benefits. There is a need to enhance such analyte monitoring systems via innovations comprising, but not limited to, improved analyte monitoring information management.

SUMMARY

One aspect of the invention may provide an analyte monitoring system including an analyte sensor, a transceiver, a display device, and a management system. The transceiver may be configured to receive sensor data from the analyte sensor and calculate analyte monitoring information. The display device may be configured to receive the analyte monitoring information from the transceiver. The management system may be configured to receive analyte monitoring information from the display device. The management system may be configured to use the analyte monitoring information to produce a comparison result. The management system may be configured to determine, based on the comparison result, whether a condition is satisfied. The management system may be configured to, in response to determining that the condition is satisfied, transmit to the display device management information associated with the received analyte monitoring information.

In some embodiments, the analyte monitoring information may include one or more performance diagnostics, and using the analyte monitoring information to produce the comparison result may include comparing the one or more performance diagnostics with one or more performance indicators. In some embodiments, the one or more performance indicators may include one or more performance thresholds, and comparing the analyte monitoring information with the one or more performance indicators may include comparing the one or more performance diagnostics with the one or more performance thresholds. In some embodiments, the management system may calculate at least one of the one or more performance indicators using one or more of (i) sensor shipment information, (ii) insertion dates of one or more sensors, (iii) removal dates of one or more sensors, and (iv) a number of days since implant of one or more sensors.

In some embodiments, the management information may include a replacement date for the sensor. In some embodiments, the management information may include a command that instructs the display device to transmit information to the transceiver.

In some embodiments, the management system may be further configured to generate compliance information based on the analyte monitoring information, and using the analyte monitoring information to produce the comparison result may include comparing the compliance information with usage protocol information. In some embodiments, the analyte monitoring information may include calibration data, the management system may be configured to generate the compliance information based on the calibration data, the usage protocol information may include one or more compliance thresholds, and comparing the compliance information with the usage protocol information may include comparing the compliance information with the one or more compliance thresholds. In some embodiments, the management information may include a command for the display device to display a compliance alert.

In some embodiments, the analyte monitoring information may include battery information. In some embodiments, using the analyte monitoring information to produce the comparison result may include comparing the battery information with a battery threshold. In some embodiments, the condition may be satisfied in response to determining that the battery voltage is below the battery threshold. In some embodiments, the management information may include an instruction for the display device to display a battery replacement alert.

In some embodiments, the analyte sensor may be a first analyte sensor, the transceiver may be a first transceiver, the display device may be a first display device, the sensor data may be first sensor data, the analyte monitoring information may be first analyte monitoring information, the comparison result may be a first comparison result, and the condition may be a first condition. In some embodiments, the analyte monitoring system may further include a second analyte sensor, a second transceiver, and a second display device. In some embodiments, the second transceiver may be configured to receive second sensor data from the second analyte sensor and calculate second analyte monitoring information. In some embodiments, the second display device may be configured to receive the second analyte monitoring information from the transceiver. In some embodiments, the management system may be further configured to receive second analyte monitoring information from the second display device. In some embodiments, the management system may be further configured to use the second analyte monitoring information to produce a second comparison result. In some embodiments, the management system may be further configured to determine, based on the second comparison result, whether a second condition is satisfied. In some embodiments, the management system may be further configured to, in response to determining that the second condition is satisfied, transmit to the second display device management information associated with the received second analyte monitoring information.

In some embodiments, the first analyte monitoring information may include one or more first performance diagnostics, the second analyte monitoring information may include one or more second performance diagnostics, the first and second analyte sensors may be part of a sensor lot, using the first analyte monitoring information to produce the first comparison result may include comparing the one or more first performance diagnostics with one or more sensor lot performance indicators, and using the second analyte monitoring information to produce the second comparison result may include comparing the one or more second performance diagnostics with the one or more sensor lot performance indicators. In some embodiments, the management system may be further configured to calculate one or more sensor lot performance diagnostics using the one or more first performance diagnostics and the one or more second performance diagnostics. In some embodiments, the management system may be further configured to modify one or more of the one or more sensor lot performance indicators using the one or more sensor lot performance diagnostics.

In some embodiments, the first analyte monitoring information may include one or more first performance diagnostics, the second analyte monitoring information may include one or more second performance diagnostics, the first and second transceivers may be part of a transceiver lot, using the first analyte monitoring information to produce the first comparison result may include comparing the one or more first performance diagnostics with one or more transceiver lot performance indicators, and using the second analyte monitoring information to produce the second comparison result may include comparing the one or more second performance diagnostics with the one or more transceiver lot performance indicators. In some embodiments, the management system may be further configured to calculate one or more transceiver lot performance diagnostics using the one or more first performance diagnostics and the one or more second performance diagnostics. In some embodiments, the management system may be further configured to modify one or more of the one or more transceiver lot performance indicators using the one or more transceiver lot performance diagnostics.

Another aspect of the invention may provide a method performed in a management system of an analyte monitoring system. The method may include the management system receiving analyte monitoring information from a display device in communication with a transceiver that is in communication with a sensor. The method may include the management system using the analyte monitoring information to produce a comparison result. The method may include the management system determining, based on the comparison result, whether a condition is satisfied. The method may include, in response to determining that the condition is satisfied, the management system transmitting, to the display device, management information associated with the received analyte monitoring information.

In some embodiments, the analyte monitoring information may include one or more performance diagnostics, and using the analyte monitoring information to produce the comparison result may include comparing the one or more performance diagnostics with one or more performance indicators. In some embodiments, the one or more performance indicators may include one or more performance thresholds, and comparing the analyte monitoring information with the one or more performance indicators may include comparing the one or more performance diagnostics with the one or more performance thresholds.

In some embodiments, the management information may include a replacement date for the sensor. In some embodiments, the management information may include a command that instructs the display device to transmit information to the transceiver.

In some embodiments, the method may further include the management system generating compliance information based on the analyte monitoring information, and using the analyte monitoring information to produce the comparison result may include comparing the compliance information with usage protocol information. In some embodiments, the analyte monitoring information may include calibration data, the compliance information may be generated based on the calibration data, the usage protocol information may include one or more compliance thresholds, and comparing the compliance information with the usage protocol information comprises comparing the compliance information with the one or more compliance thresholds. In some embodiments, the management information may include a command for the display device to display a compliance alert.

In some embodiments, the analyte monitoring information may include battery information, and using the analyte monitoring information to produce the comparison result may include comparing the battery information with a battery threshold. In some embodiments, the condition may be satisfied in response to determining that the battery information is below the battery threshold, and the management information may include an instruction for the display device to display a battery replacement alert.

In some embodiments, at least one of the one or more performance indicators may be calculated by the management system using one or more of (i) sensor shipment information, (ii) insertion dates of one or more sensors, (iii) removal dates of one or more sensors, and (iv) a number of days since implant of one or more sensors. In some embodiments, the at least one calculated performance indicator may provide a variation between sensor to sensor lots or transmitter to transmitter lots.

In some embodiments, the sensor may be a first sensor, the transceiver may be a first transceiver, the display device may be a first display device, the analyte monitoring information may be first analyte monitoring information, the comparison result may be a first comparison result, and the condition may be a first condition. In some embodiments, the method may further include the management system receiving second analyte monitoring information from the second display device. In some embodiments, the method may further include the management system using the second analyte monitoring information to produce a second comparison result. In some embodiments, the method may further include the management system determining, based on the second comparison result, whether a second condition is satisfied. In some embodiments, the method may further include the management system, in response to determining that the second condition is satisfied, transmitting to the second display device management information associated with the received second analyte monitoring information.

In some embodiments, the first analyte monitoring information may include one or more first performance diagnostics, the second analyte monitoring information may include one or more second performance diagnostics, the first and second sensors may be part of a sensor lot, using the first analyte monitoring information to produce the first comparison result may include comparing the one or more first performance diagnostics with one or more sensor lot performance indicators, and using the second analyte monitoring information to produce the second comparison result may include comparing the one or more second performance diagnostics with the one or more sensor lot performance indicators. In some embodiments, the method may further include the management system calculating one or more sensor lot performance diagnostics using the one or more first performance diagnostics and the one or more second performance diagnostics. In some embodiments, method may further include the management system modifying one or more of the one or more sensor lot performance indicators using the one or more sensor lot performance diagnostics.

In some embodiments, the first analyte monitoring information may include one or more first performance diagnostics, the second analyte monitoring information may include one or more second performance diagnostics, the first and second transceivers may be part of a transceiver lot, using the first analyte monitoring information to produce the first comparison result may include comparing the one or more first performance diagnostics with one or more transceiver lot performance indicators, and using the second analyte monitoring information to produce the second comparison result may include comparing the one or more second performance diagnostics with the one or more transceiver lot performance indicators. In some embodiments, the method may further include the management system calculating one or more transceiver lot performance diagnostics using the one or more first performance diagnostics and the one or more second performance diagnostics. In some embodiments, the method may further include the management system modifying one or more of the one or more transceiver lot performance indicators using the one or more transceiver lot performance diagnostics.

Another aspect of the invention may provide a method performed in a management system. The method may include the management system collecting information from one or more analyte monitoring sources. The method may include the management system preparing an information record based on the collected information. The method may include the management system transmitting a post market information record to a display device.

In some embodiments, the information record may be a post marketing analysis chart that specifies, for a plurality of sensors and corresponding transceivers, one or more of a geographic distribution, insertion date, number of days since implant, device type, device OS, and firmware version.

Another aspect of the invention may provide a management system that may include a processor and a non-transitory computer readable medium coupled to the processor. The non-transitory computer readable medium may include instructions, which when executed by the processor may cause the processor to receive analyte monitoring information from a display device in communication with a transceiver that is in communication with a sensor. The instructions may cause the processor to compare the analyte monitoring information with one or more performance indicators to produce a comparison result. The instructions may cause the processor to determine, based on the comparison result, whether a condition is satisfied. The instructions may cause the processor to, in response to determining that the condition is satisfied, transmit, to the display device, management information associated with the received analyte monitoring information.

Another aspect of the invention may provide a management system that may include a processor and a non-transitory computer readable medium coupled to the processor. The non-transitory computer readable medium may include instructions, which when executed by the processor, may cause the processor to collect information from one or more analyte monitoring sources. The instructions may cause the processor to prepare an information record based on the collected information. The instructions may cause the processor to transmit a post market information record to a display device.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
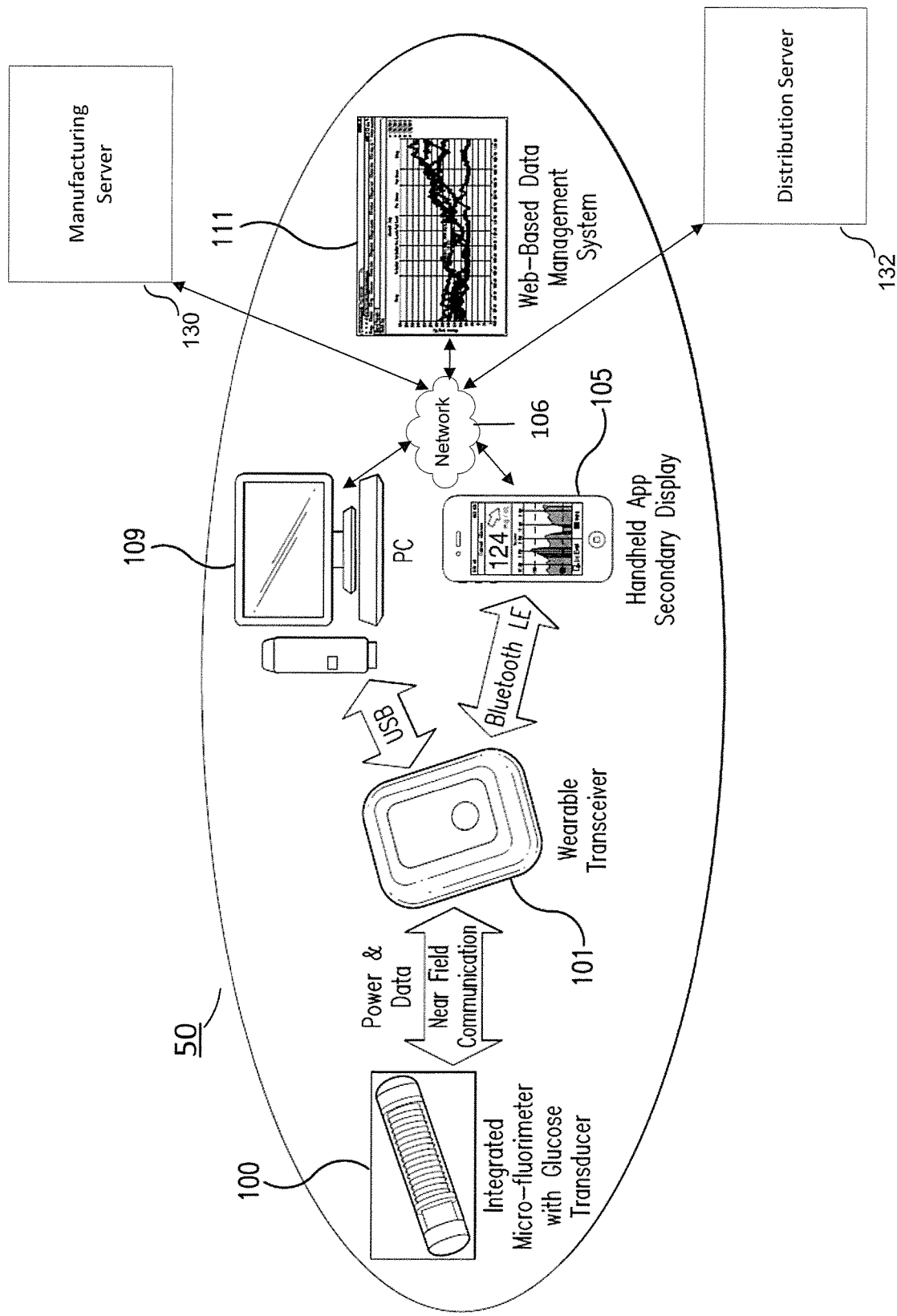
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transceiver 101, and display devices such as a handheld device (e.g., smart phone or tablet 105;

personal computer 109, etc.). In some embodiments, the sensor 100 may be small, fully subcutaneously implantable sensor measures analyte (e.g., glucose) concentrations in a medium (e.g., interstitial fluid) of a living animal (e.g., a living human). However, this is not required, and, in some alternative embodiments, the sensor 100 may be a partially implantable (e.g., transcutaneous) sensor or a fully external sensor.

In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensor 100 via one or more wired connections. In some non-limiting embodiments, the transceiver 101 may be a smartphone (e.g., an NFC-enabled smartphone). In some embodiments, the transceiver 101 may communicate information (e.g., one or more analyte concentrations) wirelessly (e.g., via a Bluetooth™ communication standard such as, for example and without limitation, Bluetooth Low Energy) to a hand held application running on a display device 105 (e.g., smartphone). In some embodiments, information can be downloaded from the transceiver 101 through a Universal Serial Bus (USB) port. In some embodiments, the analyte monitoring system 50 may include a web interface for plotting and sharing of uploaded data. In some embodiments, display devices 105 and 109 may run an application such as a mobile medical application (MMA).

In some embodiments, the analyte monitoring system 50 may include a web-based data management system 111 that communicates with one or more of display devices 105 and 109 over any appropriate network 106 known to one of ordinary skill in the art such as the Internet, 3G, 4G, 5G, local area network (LAN), wireless local area network (WLAN), virtual private network (VPN). In some embodiments, the management system 111 may comprise one or more servers operating as a cloud management system. The management system 111 may also be in communication over the network 106 with one or more systems or servers such as, for example and without limitation, one or more management servers 130 and/or one or more distribution servers 132. In some non-limiting embodiments, the one or more management servers 130 and/or the one or more distribution servers 132 may be external to the analyte monitoring system 50. In some alternative embodiments, the analyte monitoring system 50 may include the one or more management servers 130 and/or the one or more distribution servers 132. In some alternative embodiments, the management system 111 may include the one or more management servers 130 and/or the one or more distribution servers 132.

As an example of communication flow path between the wearable transceiver 101 and management system 111, in some embodiments, the wearable transceiver 101 may receive sensor data (e.g., measurement data such as, for example and without limitation, one or more light measurements and one or more temperature measurements) from the sensor 100. In some embodiments, the transceiver 101 may calculate analyte monitoring information and forward some or all of the analyte monitoring information to one or more of display devices 105 and 109. In some embodiments, the analyte monitoring information may include one or more analyte levels (e.g., one or more glucose concentrations), one or more analyte level rates of change, and/or one or more alerts, alarms, and/or notifications. In some embodiments, one or more of the display devices 105 and 109 may convey some or all of the analyte monitoring information to the management system 111. As another example of a communication flow path, the management system 111 may transmit information to one or more of the display devices 105 and 109, which may transmit to the wearable transceiver 101 and/or the sensor 100.

In some alternative embodiments, the transceiver 101 may forward the received sensor data to one or more of the display device 105 and 109, and one or more of display device 105, display device 109, and management system 111 may calculate the analyte monitoring information. In some other alternative embodiments, one or more of the display devices 105 and 109 (e.g., an NFC-enabled smartphone) may communicate directly with the sensor 100, receive the sensor data, and calculate the analyte monitoring information.

In some embodiments, the management system 111 may gather device information from one or more of the display device 105 (e.g., smartphone), display device 109, and transceiver 101. In some embodiments, the management system 111 may additionally or alternatively gather device information from one or more other wearable devices (e.g. one or more of an insulin pen and Blood glucose meter), which may communicate within the monitoring system 50. In some embodiments, the gathered information may provide information regarding the geographic usage of the analyte monitoring system 50. In some non-limiting embodiments, the management system 111 may include, for each analyte monitoring system 50, one or more of an identification of the analyte monitoring system 50 and/or patient (Sys ID), an identification of the sensor 100 (Sensor ID), a date and time of insertion of the sensor 100 (Insert Time), an identification of the transceiver 101 (Tran ID), a transceiver firmware version (FW Version), a current phase of operation of the analyte monitoring system 50, a calibration start date, a device type of the display device 105, a type of operating system of the display device 105 (OS Type), an OS version for the OS of the display device 105 (OS Version), and a version of the app (e.g., MMA) being executed by the display device 105 (App Version). A non-limiting example of information records that may be stored on the management system 111 and may be created based on information collected by the management system 111 is show below in Table 1.

TABLE 1

| Sys ID | Sensor ID | Insert Time | Tran ID | FW Version | Current Phase | Device Type | OS Type | OS Version | App Version |
|---|---|---|---|---|---|---|---|---|---|
| 10276 | 16745218 | Jun. 20, 2017 13:00:00 | 6802 | 6.21.04 | Warm up | iPhone 9 | iOS | 10.3.2 (14F89) | 5.2.303 |
| 10243 | 16745244 | Jun. 20, 2017 14:00:00 | 6806 | 6.21.04 | Warm up | Android | Android | 7.0 (24) | 1.0.307 |
| 10238 | 16745324 | May 19, 2017 09:00:00 | 6812 | 6.21.04 | Daily Calibration | iPhone 9 | iOS | 10.3.2 (14F89) | 5.2.03 |

In some embodiments, the sensor 100 may have replaced a previous sensor 100 and/or may be replaced by a new sensor 100, and the transceiver 101 may have replaced a previous transceiver 101 and/or may be replaced by a new transceiver 101. Accordingly, in some embodiments, the information records stored on the management system 111 may additionally or alternatively include, for each analyte monitoring system 50, one or more of (i) an identification and insertion date and time of all sensors 100 that have been used in the analyte monitoring system 50 and (ii) an identification and calibration start date of all transceivers 101 that have been used in the analyte monitoring system 50.

In some embodiments, the information records stored on the management system 111 may additionally or alternatively include, for each analyte monitoring system 50, a list of the alerts, alarms, and/or notifications generated by the analyte monitoring system 50 and a date and time that the alerts, alarms, and/or notifications were generated. In some embodiments, the information records stored on the management system 111 may additionally or alternatively include, for each analyte monitoring system 50, user preferences.

In some embodiments, the user preferences may be entered into the analyte monitoring system 50 using the app being executed by the display device 105. In some embodiments, the user preferences may include one or more of unit of measurement preference (e.g., mg/dL or mmol), a low analyte level alarm threshold (e.g., 80 mg/dL), a high analyte level alarm threshold (e.g., 200 mg/dL), a low analyte level alert threshold (e.g., 70 mg/DL), a high analyte level alert threshold (e.g., 140 mg/dL), a predicted analyte level time period (e.g., 30 minutes), and an analyte level rate of change alarm threshold (e.g., 5 mg/dL per minute).

In some embodiments, the information records stored on the management system 111 may additionally or alternatively include, for each analyte monitoring system 50, logs from the transceiver 101. A non-limiting example of transceiver logs that may be stored on the management system 111 and may be used for diagnostic purposes is shown below in Table 2.

TABLE 2

| Log Name | Modified Date | File Size |
|---|---|---|
| 0DMS_0000_21567_00_0002017.12.28T11.03.37.csv | Dec. 28, 2017 | 1.3 MB |
| 0DMS_0000_21546_00_0002017.12.27T02.54.31.csv | Dec. 27, 2017 | 811.7 KB |
| 0DMS_0000_21100_00_0002017.12.22T11.25.51.csv | Dec. 22, 2017 | 99 KB |

In some embodiments, one or more of the display devices 105 and 109 may execute an application (e.g., a mobile medical application (MMA)) that communicates with and collects information from the transceiver 101, and the application may convey the collected information to the management system 111. Furthermore, in some embodiments, the transceiver 101 may receive one or more raw sensor measurements (e.g., light and temperature measurements) from the sensor 100 and calculates one or more analyte levels (e.g., glucose concentrations) based on at least the received raw sensor measurements. In some embodiments, the transceiver 101 may additionally use the calculated analyte levels to calculate analyte level trends (e.g., the rate at which the analyte level is increasing or decreasing).

In some embodiments, the transceiver 101 may calculate one or more performance diagnostics (e.g., based on raw sensor measurements). In some non-limiting embodiments, the transceiver 101 may calculate one or more performance diagnostics in the manner described in U.S. application Ser. No. 15/786,954, filed Oct. 18, 2017, the entire contents of which are incorporated herein by reference. In some embodiments, the transceiver 101 may additionally or alternatively generate one or more of analyte-related and analyte unrelated alerts, alarms, and/or notifications.

In some embodiments, the analyte monitoring information received by the data management system 111 may include one or more performance diagnostics. In some embodiments, the information records stored on the management system 111 may additionally or alternatively include, for each analyte monitoring system 50, one or more of an identification of the user (User ID), an identification of the sensor 100 (Sensor ID), the date and time of insertion of the sensor 100 (Insert Time), a lot number of the sensor 100 (Lot #), an identification of the transceiver 101 (Tran ID), one or more received performance diagnostics (e.g., PD1-PD5), and the date and time that the one or more performance diagnostics were generated or received (PD Date). A non-limiting example of information records that may be stored on the management system 111 and may be created based on information collected by the management system 111 is show below in Table 3.

TABLE 3

| User ID | Sensor ID | Insert Time | Lot # | Tran ID | PD1 | PD2 | PD3 | PD4 | PD5 | PD Date |
|---|---|---|---|---|---|---|---|---|---|---|
| 468 | 29580 | Nov. 8, 2016 17:12:00 | 55 | 6421 | 1.000 | 1.000 | 1.000 | 1.000 | 1.000 | Dec. 29, 2017 16:00:00 |
| 366 | 30502 | Nov. 20, 2016 16:08:00 | 55 | 7024 | 1.000 | 1.000 | 1.000 | 1.000 | 1.000 | Dec. 29, 2017 16:30:00 |
| 160 | 29579 | Nov. 8, 2016 18:02:00 | 55 | 6459 | 0.000 | 0.961 | 1.000 | 1.000 | 0.855 | Dec. 29, 2017 17:00:00 |

In some embodiments, the received one or more performance diagnostics may be compared against one or more performance indicators to determine if any action is required. In some embodiments, the action may be, for example and without limitation, informing the patient of the need to schedule a sensor explant and new sensor insertion based on the comparison of the one or more performance diagnostics and the one or more performance indicators. For example, in some non-limiting embodiments, the comparison of one or more of the performance diagnostics PD1-PD5 associated with Sensor ID 29579 in Table 3 above against one or more performance indicators may indicate that the sensor 100 identified by Sensor ID 29579 needs to be replaced, and the management system 111 may notify the user (e.g., by conveying a notification to the display device 105). In some embodiments, if one or more of the performance diagnostics falls below one or more performance thresholds, the management system 111 may transmit an instruction to one or more of the display devices 105 and 109 to display or sound an alert, warning, or notification to indicate to the user that a near term sensor replacement is required. For example, the notification may be used to schedule future replacement appointments with a physician. For another example, notification may additionally or alternatively be used to contact patients and preset their next sensor schedule.

In some embodiments, the management system 111 may receive and review one or more of (i) sensor data received by the transceiver 101 from the sensor 100, and (ii) the analyte monitoring information. In some embodiments, the management system 111 may receive the sensor data and analyte monitoring information via one of display devices 105 and 109. In some embodiments, the management system 111 may use one or more of the sensor data and the analyte monitoring information to provide updated information that can be pushed back to the transceiver 101 to improve the performance of the analyte monitoring system 50. In some embodiments, a dynamic update of the conversion function used by the transceiver 101 (and/or the display device 105 or 109) to calculate analyte concentrations based on the sensor data received from the sensor 100 may be performed with information received on the management system 111. For example, in some non-limiting embodiments, the management system 111 may provide one or more parameters to update one or more parameters of the conversion function. In some non-limiting embodiments, the management system 111 may store historical data for a user. The historical data may include one or more of (i) past calculated analyte levels, (ii) past user-entered calibration information (e.g., reference analyte level measurements such as finger-stick measurements), (iii) past analyte level trends, and (iv) past user-entered event information. The management system 111 may analyze the historical information for the user and provide updated parameters that personalize the conversion function for the specific user. In some embodiments, the personalized conversion function may provide more accurate analyte levels. For another example, the management system 111 may additionally or alternatively provide one or more sensor parameters. In some embodiments, the transceiver 101 may use the one or more sensor parameters to update one or more sensor parameters (e.g., the gain of an amplifier of the sensor 100 and/or the drive current of a light source of the sensor 100). In some embodiments the updated sensor parameters may prevent an improper sensor replacement alert.

In some embodiments, when an application (e.g., a mobile medical application) executed by one or more of display devices 105 and 109 connected with the transceiver 101, the application may receive or pull event-based information from the transceiver 101 and may use the event-based information for real-time diagnosis. For example, in some embodiments, the transceiver 101 may issue a battery alert. When the application receives the battery alert, the application may send an instruction to the transceiver 101 to transmit information with respect to a battery of the transceiver 101 (e.g., information indicating a voltage of a battery of the transceiver 101). In some embodiments, the application may receive the requested battery information and convey the battery information to the management system 111. In some embodiments, the management system 111 may receive the conveyed battery information and compare the battery information with a battery threshold (e.g., a battery voltage threshold). In some embodiments, if the battery information is below the battery threshold, the management system 111 may transmit an instruction to one or more of the display devices 105 and 109 to display or sound an alert indicating that replacement of the battery of the transceiver 101 is required.

In some embodiments, the management system 111 may receive one or more of sensor lot information and transceiver lot information (e.g., from the manufacturing server 130). In some embodiments, the sensor lot information may identify groups of sensors that were manufactured together. In some embodiments, the transceiver lot information may identify groups of transceivers that were manufactured together. In some embodiments, the management system 111 may generate or modify one or more performance indicators, which are compared to one or more received performance diagnostics, based on the received lot information. In some non-limiting embodiments, one or more performance indicators may be used for all sensors of one or more sensors lots or all transceivers of one or more transceiver lots.

In some embodiments, the management system 111 may receive performance diagnostics regarding the performance of multiple sensors and/or multiple transceivers (e.g., from one or more transceivers 101 via one or more display devices 105 or 109). In some embodiments, the management system 111 may gather one or more performance diagnostics regarding the performance of the sensors of one or more sensor lots and/or the transceivers of one or more transceiver lots. For example, in some non-limiting embodiments, the management system 111 may calculate one or more sensor lot performance diagnostics indicative of the performance of a particular sensor lot based on two or more performance diagnostics regarding the performance of two or more sensors from the sensor lot. In some embodiments, the management system 111 may calculate the one or sensor lot performance diagnostics by combining (e.g., averaging) the two or more performance diagnostics regarding the performance of the two or more sensors from the sensor lot. In some embodiments, the sensor lot performance diagnostic may be indicative of how well sensors of the sensor lot as a whole performed relative to sensors of other sensor lots. In some embodiments, the management system 111 may use one or more sensor lot performance diagnostics about a particular sensor lot to modify or update one or more performance indicators applicable to the sensors of the sensor lot.

Figure 2:
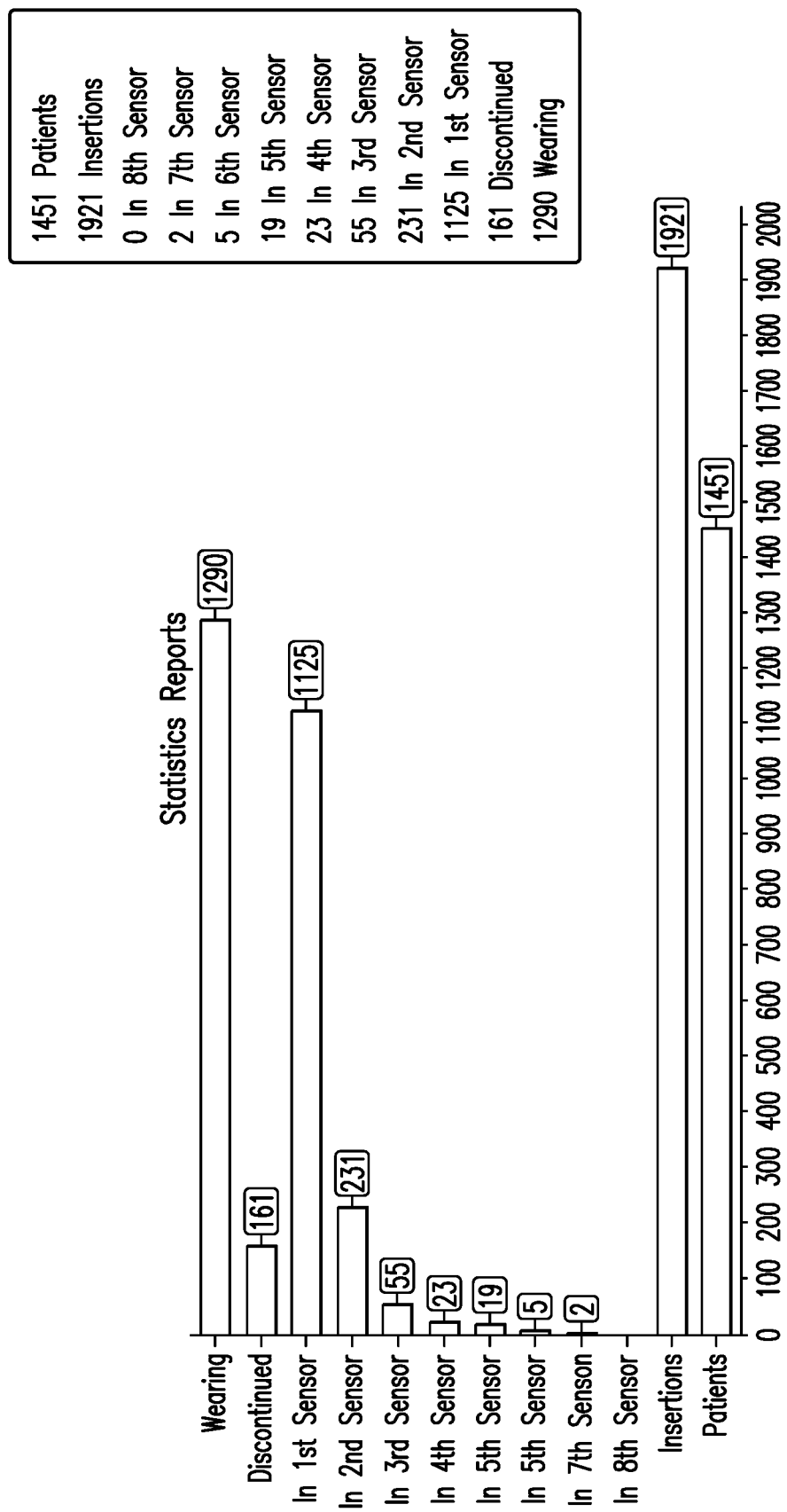
FIG. 2 illustrates an example post market statistics report generated by a data management system embodying aspects of the invention.
Figure 3:
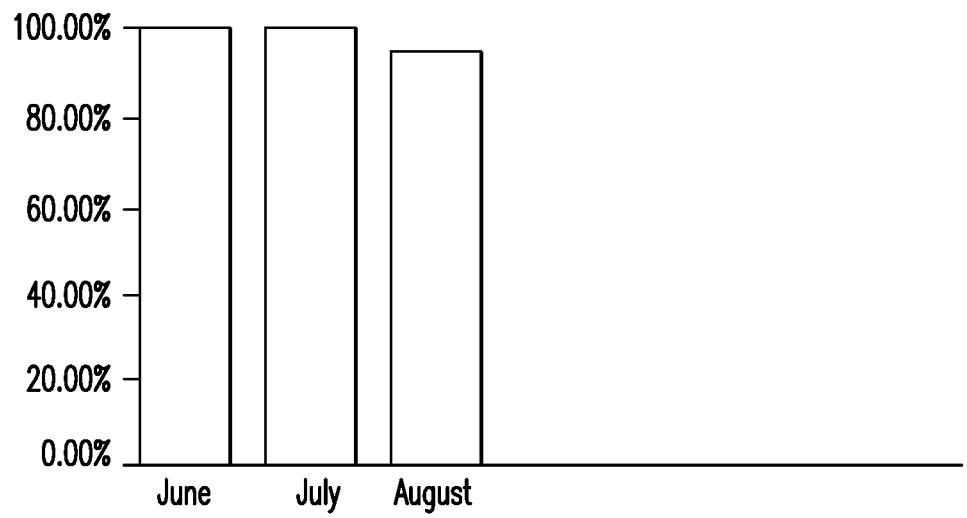
FIG. 3 illustrates an example compliance report generated the data management server embodying aspects of the present invention.
Figure 3:
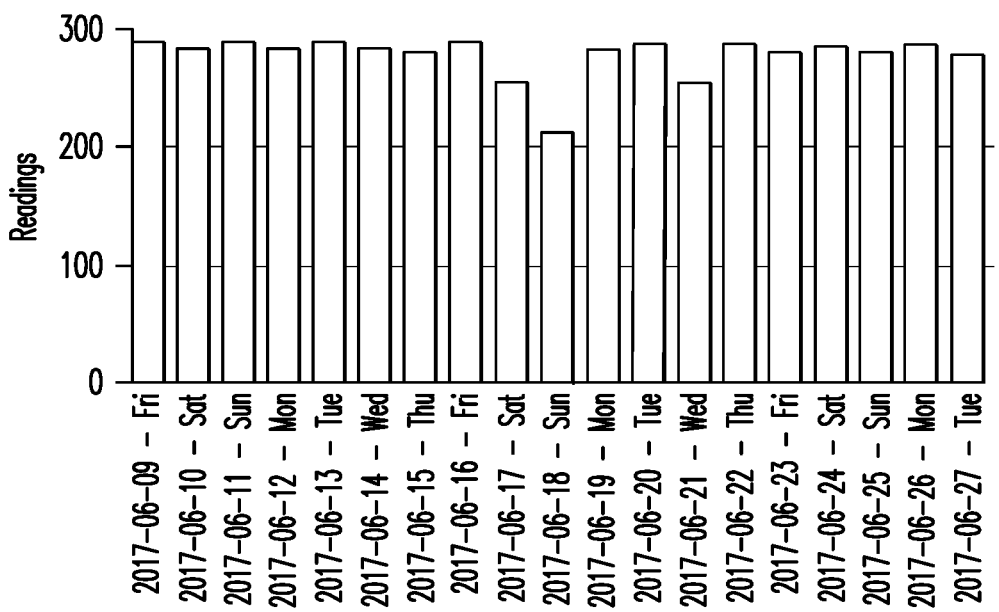

Similarly, in some non-limiting embodiments, the management system 111 may calculate one or more transceiver lot performance diagnostics indicative of the performance of a particular transceiver lot based on two or more performance diagnostics regarding the performance of two or more transceivers from the transceiver lot. In some embodiments, the management system 111 may calculate the one or transceiver lot performance diagnostics by combining (e.g., averaging) two or more performance diagnostics regarding the performance of the two or more transceivers from the transceiver lot. In some embodiments, the transceiver lot performance diagnostic may be indicative of how well transceivers of the transceiver lot as a whole performed relative to other transceiver lots. In some embodiments, the management system 111 may use one or more transceiver lot marketing information, such as, for example and without limitation, a post-marketing chart. FIG. 2 illustrates an example of a post marketing chart that the management system 111 may create using information that the management system 111 gathers. In some embodiments, the management system 111 may transmit the post marketing chart for display on one or more of display devices 105 and 109. In some non-limiting embodiments, the management system 111 may additionally or alternatively generate post-marketing information records, such as, for example and without limitation, the post-marketing information including, for each analyte monitoring system 50, one or more of: an identification of the analyte monitoring system 50 (Sys ID), an identification of the user/patient (User ID), an identification of the sensor 100 (Sensor ID), a date and/or time of insertion of the sensor 100 (Insert Date), a date and/or time of removal of the sensor 100 if the sensor 100 has been removed (Remove Date), an expected or predicted date and/or time of removal of the sensor 100 (Expected Remove Date), an identification of whether a sensor 100 is implanted in the user (In Use?), the number of sensors 100 that have been implanted (e.g., sequentially) in the user (Sen CNT), the number of days the sensor has been implanted in the user (Sensor Days), an identification of the transceiver 101 (Tran ID), an identification of the clinic and/or location where the sensor 100 was implanted (Clinic (Loc)), and an identification of a physician that implanted or oversaw implantation of the sensor 100 (Phys). In some embodiments, the management system 111 may generate the post marketing information records based on information gathered by the management system 111. In some embodiments, the post marketing information records may correlate a particular geographic location with a corresponding sensor ID and transceiver ID, as well as indicate a number of days a sensor has been worn, and an expected removal date. A non-limiting example of post-marketing information records that may be generated by the management system 111 is shown in Table 4 below.

TABLE 4

| Sys ID | User ID | Sensor ID | Insert Date | Remove Date | Expected Remove Date | In Use? | Sen CNT | Sensor Days | Tran ID | Clinic (Loc) | Phys |
|---|---|---|---|---|---|---|---|---|---|---|---|
| 69 | 197-0195 | 27866 | Jun. 21, 2016 | Sep. 19, 2016 | Sep. 26, 2016 | No | 1 | 90 | 27866 | Clinic A (Sweden) | Dr. A |
| 79 | 197-0196 | 34893 | Jun. 6, 2017 | — | Sep. 27, 2016 | Yes | 5 | 190 | 34893 | Clinic B (Sweden) | Dr. B | performance diagnostics to modify or update one or more performance indicators applicable to the transceivers of the transceiver lot.

In some embodiments, the one or more sensor lot performance diagnostics and/or one or more transceiver lot performance diagnostics may be used to trace underperforming sensor or transmitter lots back to a manufacturer to determine whether the underperformance indicates a systemic issue in a manufacturing process.

In some embodiments, the management system 111 may gather information from one or more applications (e.g., MMAs) running on one or more of display devices 105 and 109, one or more transceivers 101, one or more manufacturing servers 130, and/or one or more distribution servers 132 to automatically track one or more of sensor shipment, sensor insertion, sensor removal, and number of sensor days since implant. In some embodiments, the management system 111 may generate, from the gathered information, post In some non-limiting embodiments, the management system 111 may generate compliance information indicative of the extent to which a user is using an analyte monitoring system 50 in accordance with usage protocols. In some embodiments, the usage protocols may relate to how a user should be using the analyte monitoring system 50. For example, in some non-limiting embodiments, the usage protocols may relate to one or more of: (i) the frequency with a user is supposed to calibrate the analyte monitoring system 50 (e.g., by entering calibration information such as, for example and without limitation, a reference analyte measurement), (ii) the extent to which a user is keeping a monitored analyte level within a target range, and (iii) the extent to which a user should be using the analyte monitoring system 50 (e.g., by enabling the transceiver 101 to receive analyte data from an implanted sensor 100 such as, for example and without limitation, by wearing or swiping the transceiver 101). In some embodiments, the usage protocols may relate to how a user is using the analyte monitoring system 50. In some embodiments, the compliance information may relate to one or more of (i) the frequency with a user is calibrating the analyte monitoring system 50, (ii) the extent to which a user is keeping a monitored analyte level within a target range, and (iii) the extent to which a user is using the analyte monitoring system 50 (e.g., by enabling the transceiver 101 to receive analyte data from an implanted sensor 100 such as, for example and without limitation, by wearing or swiping the transceiver 101, which enables the transceiver 101 to calculate analyte levels for the user).

In some embodiments, the management system 111 may receive and store calibration data for one or more analyte monitoring systems 50, and the compliance information may include the calibration data. In some embodiments, the calibration data may include information about when calibrations of the analyte monitoring system 50 occurred. In some embodiments, the calibrations of the analyte monitoring system 50 may occur in response to a user entering one or more reference analyte measurements, such as, for example and without limitation, self-monitoring blood glucose measurements, into the analyte monitoring system 50. In some non-limiting embodiments, a user may enter the calibration information using the MMA being executing on a display device 105. In some embodiments, the management system 111 may use the calibration data to generate one or more calibration compliance metrics (e.g., for each analyte monitoring system 50, one or more of (i) the number of calibration entered in the analyte monitoring system 50 in a time period, such as for example and without limitation, the last 3 days, the last 24 hours, and/or the last 7 days and (ii) the total number of calibrations of the analyte monitoring system 50, and (iii) the last date of synchronization). A non-limiting example of calibration compliance information stored in the management system 111 is shown in Table 5 below. As shown in Table 5, the calibration compliance information can be correlated with a corresponding transceiver ID (Tran ID) and/or sensor ID and may include one or more of a last calibration date (Last Cal Date), a number of calibrations in the last 24 hours (# of Cals (Last 24 Hours)), a number of calibrations in the last 3 days (# of Cals (Last 3 Days)), a number of calibrations in the last 7 days (# of Cals (Last 7 Days)), a total number of calibrations (# of Cals (Total)), and date of last synchronization (Last Sync Date).

TABLE 5

| Sensor ID | Tran ID | Last Cal Date | # of Cals (Last 24 Hours) | # of Cals (Last 3 Days) | # of Cals (Last 7 Days) | # of Cals (Total) | Last Sync Date |
|---|---|---|---|---|---|---|---|
| 7679 | 20404 | Nov. 14, 2017 | 0 | 0 | 0 | 19 | Nov. 14, 2017 |
| 31140 | 7022 | Mar. 12, 2017 | 0 | 0 | 0 | 207 | Mar. 12, 2017 |
| 15352 | 20890 | Dec. 23, 2017 | 0 | 0 | 9 | 17 | Dec. 24, 2017 |

In some embodiments, the management system 111 may use the compliance information to trigger an alert to the clinic or to the user when the compliance information indicates that compliance has fallen below one or more compliance thresholds. As an example, the management system 111 may include a minimum calibration compliance threshold that indicates a minimum number of calibrations that are required to be performed within a time period (e.g., 3 days). If the management system 111 receives information from the display device 105 and/or 109 indicating that the number of calibrations performed for an analyte monitoring system 50 is below the compliance threshold, the management system 111 may transmit an instruction to one or more of the display device 105 and 109 to display or sound an alert indicating that the use is not complying with calibration requirements.

In some embodiments, the compliance information may include one or more of an identification of a user or patient (User ID), an identification of the transceiver 101 (Tran ID), an estimated Hemoglobin A1c (HbA1c) value (Estimated A1C), an average sensor analyte level calculated by the analyte monitoring system 50 (Avg Glucose), a highest sensor analyte level calculated by the analyte monitoring system 50 (High Glucose), a lowest sensor analyte level calculated by the analyte monitoring system 50 (Low Glucose), an average number of daily calibrations (Avg Daily Cals), an amount of time that the user has used the analyte monitoring system (Wear Time), an amount of time that the user's calculated analyte level has been within a target analyte level range (e.g., 70-180 mg/dL) (Time in Target), an amount of time that the user's calculated analyte level has been low (e.g., below 60 mg/dL) (Low Time), and an amount of time that the user's calculated analyte level has been high (e.g., above 250 mg/dL) (High Time). A non-limiting example of calibration compliance information stored in the management system 111 is shown in Table 6 below.

TABLE 6

| User ID | Tran ID | Estimated A1C | Avg Glucose | High Glucose | Low Glucose | Avg Daily Cals | Wear Time | Time in Target | Low Time | High Time |
|---|---|---|---|---|---|---|---|---|---|---|
| 10704 | 20575 | — | 173 | 386 | 42 | 2.1 | 97.38 | 55.01 | 4.16 | 40.83 |

In some embodiments, the compliance information may include one or more of an identification of the sensor 100 (Sensor ID), an identification of the transceiver 101 (Tran ID), a type of operating system of the display device 105 (OS Type), a number of times the transceiver 101 has determined that the sensor 100 has failed an operational check (Sensor Check), a number of times that the transceiver 101 has detected an amount of ambient light that exceeds an ambient light threshold (Ambient Light), a number of times that a calibration of the analyte monitoring system 50 expired before a new reference measurement was received (Cal Exp), a number of times that the transceiver 101 did not detect the sensor 100 (No Sensor Detected), a number of times the transceiver 101 detected a temperature higher than a threshold temperature (High Tran Temp), a number of times the transceiver 101 was not connected to the display device 105 (Tran Disconnect), a number of times that the sensor of the analyte monitoring system 50 has been replaced (Sensor RPL), a number of times that display of analyte levels as been suspended, a number of times that the charge stored in the battery of the transceiver 100 went below a battery threshold, and a number of times that the battery of the transceiver 100 was replaced.

prepare a post market analysis chart such as, for example and without limitation, the post marketing analysis chart illustrated in FIG. 2, and/or the post market analysis information record shown in Table 4 above. The process may include a step 1204 in which the management system 111 transmits some or all of the post market information to the display device 105 and/or 109. As an example, when the display device 105 and/or 109 receives the post market information, a post market analysis chart (see, e.g., FIG. 2) or the post market analysis information records (see, e.g., Table 4) may be displayed.

Figure 6:
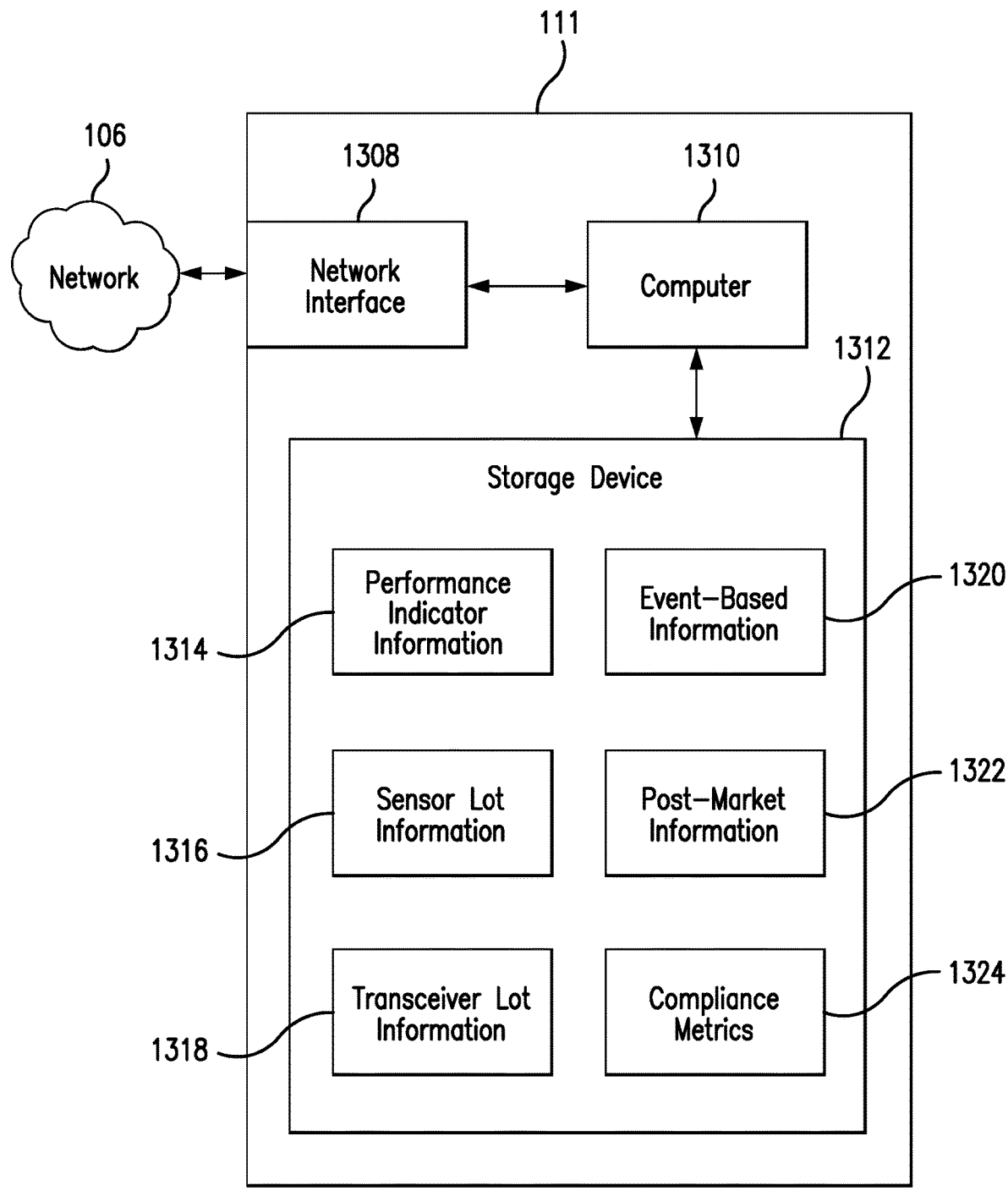
FIG. 6 illustrates a block diagram of a management system of the analyte monitoring system according to some embodiments.

FIG. 6 is a schematic view of a non-limiting embodiment of the management system 111 illustrated in FIG. 1. As illustrated in FIG. 6, in some embodiments, the management system 111 may include one or more of a network interface 1308, a computer 1310, and a storage device 1312. The network interface 1308 may be connected to the network 106. The network interface 1308 may facilitate transmission

TABLE 7

| Sensor ID | Tran ID | OS Type | Sensor Check | Ambient Light | Cal Exp | No Sensor Detected | High Tran Temp | Tran Disconnect | Sensor RPL |
|---|---|---|---|---|---|---|---|---|---|
| 27669 | 50259 (2) | Ansroid | 0 | 0 | 0 | 0 | 0 | 7 | 0 |
| 36862 | 50258 (2) | Apple | 0 | 0 | 0 | 0 | 0 | 1 | 0 |
| 36891 (2) | 50255 (3) | Android | 0 | 0 | 0 | 8 | 0 | 11 | 0 |

Figure 4:
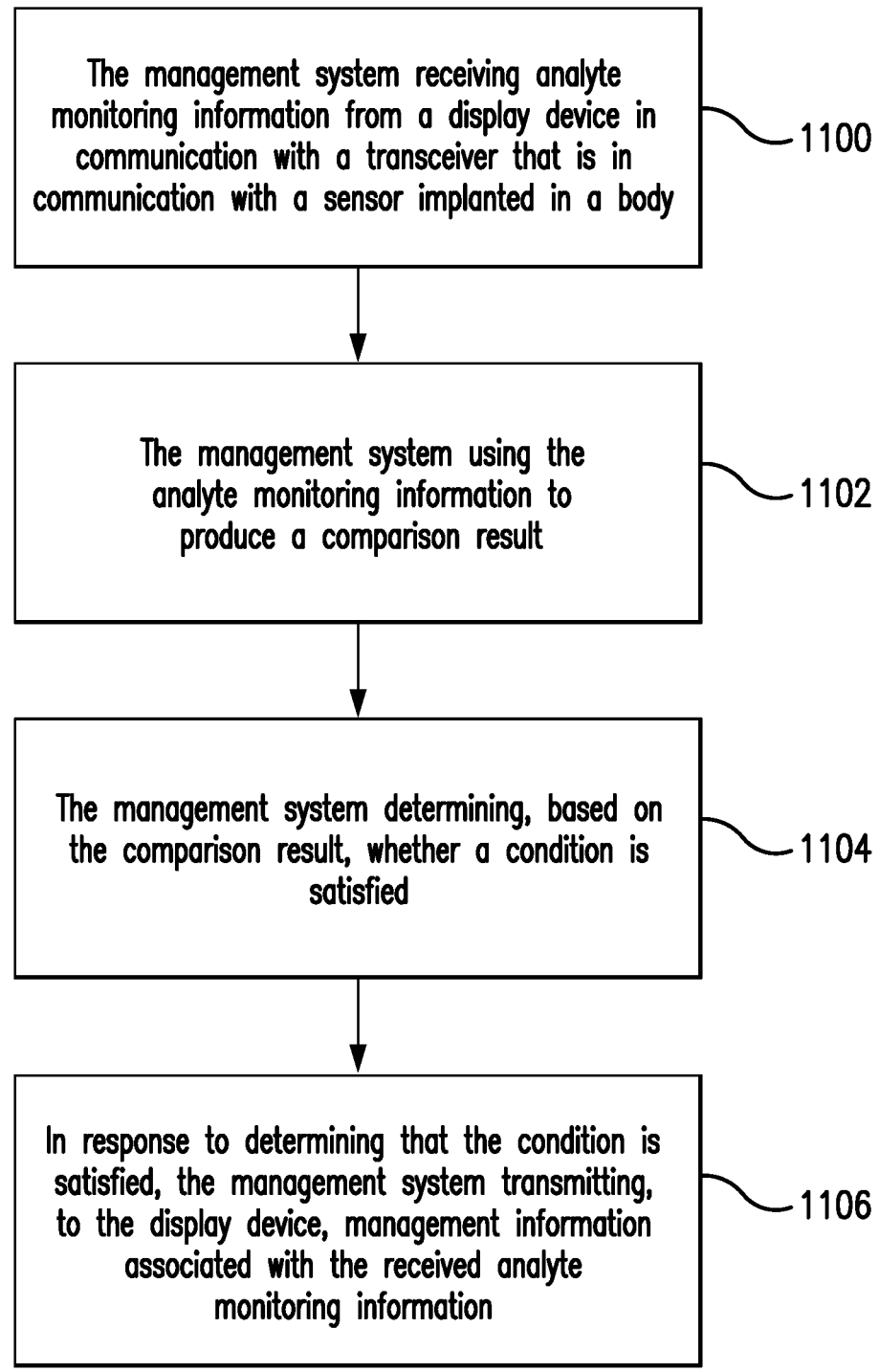
FIG. 4 is a flow chart illustrating a data management system process embodying aspects of the invention.

FIG. 4 illustrates an embodiment of a process that may be performed by the management system 111 according to some non-limiting embodiments. The process may include a step 1100 in which the management system 111 receives analyte monitoring information (e.g., from a display device 105 or 109 that is in communication with a transceiver 101 that is in communication with a sensor 100). The process may include a step 1102 in which the management system 111 uses the analyte monitoring information to produce a comparison result. For example, in step 1102, the management system 111 may compare one or more performance diagnostics in the received analyte monitoring information with one or more performance indicators. For another example, in step 1102, the management system 111 may additionally or alternatively compare compliance information (e.g., generated based on the received analyte monitoring information) with usage protocol information. In some non-limiting embodiments, the process may include a step 1104 in which the management system 111 determines, based on the comparison result, whether a condition is satisfied. The process may include a step 1106 in which, in response to determining that the condition is satisfied, the management system transmits, to the display device, management information associated with the received sensor.

Figure 5:
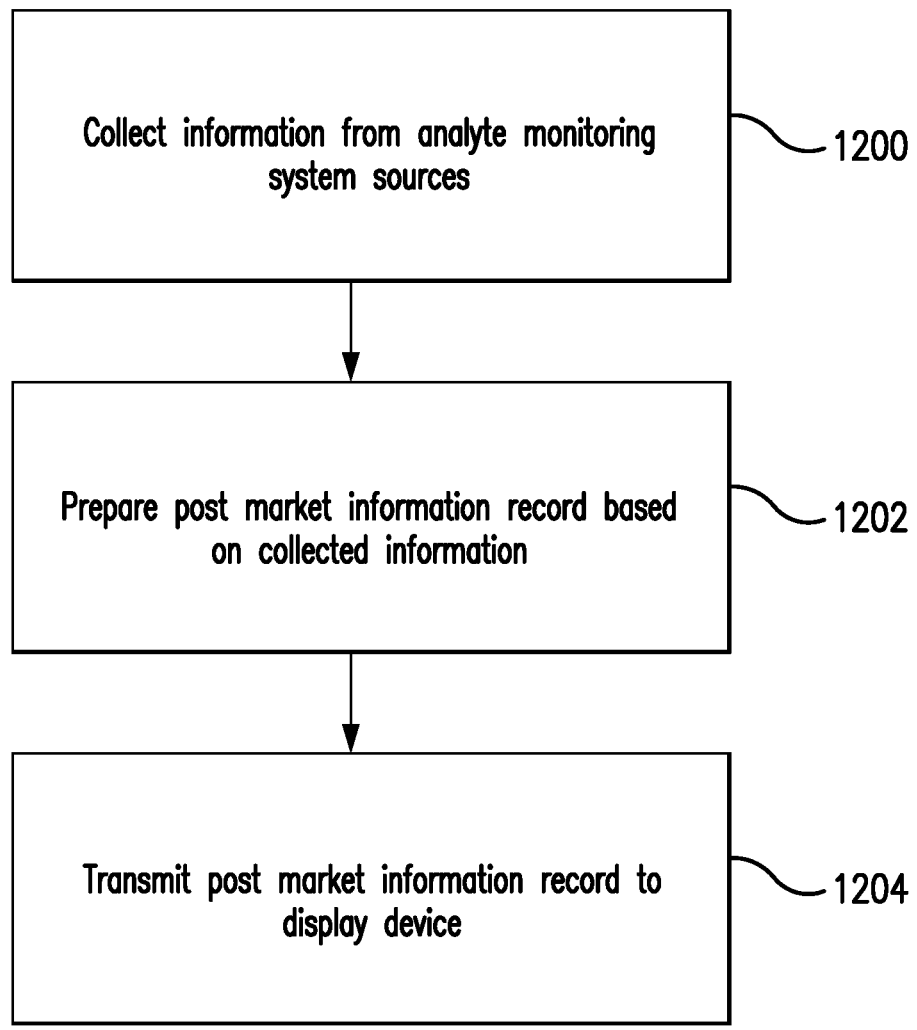
FIG. 5 is a flow chart illustrating another data management system process embodying aspects of the invention.

FIG. 5 illustrates an embodiment of another process that may additionally or alternatively be performed by the management system 111. The process may include a step 1200 in which the management system 111 collects information from one or more analyte monitoring system sources such as, for example and without limitation, transceiver 101, display devices 105 and 109, manufacturing server 130, distribution server 132, etc. The process may include a step 1202 in which the management system 111 prepares post market information based on collected information. As an example, in step 1202, the management system 111 may of data from the computer 1310 over the network 106 and receipt of information from the network 106 to the computer 1310.

In some embodiments, the storage device 1312 may be a non-volatile storage device. In some embodiments, the storage device 1312 may store one or more of the aforementioned performance indicator information 1314, sensor lot information 1316, transceiver lot information 1318, event based information 1320, post market information 1322, compliance metrics 1324, or any other information utilized in the analyte monitoring system 50.

Figure 7:
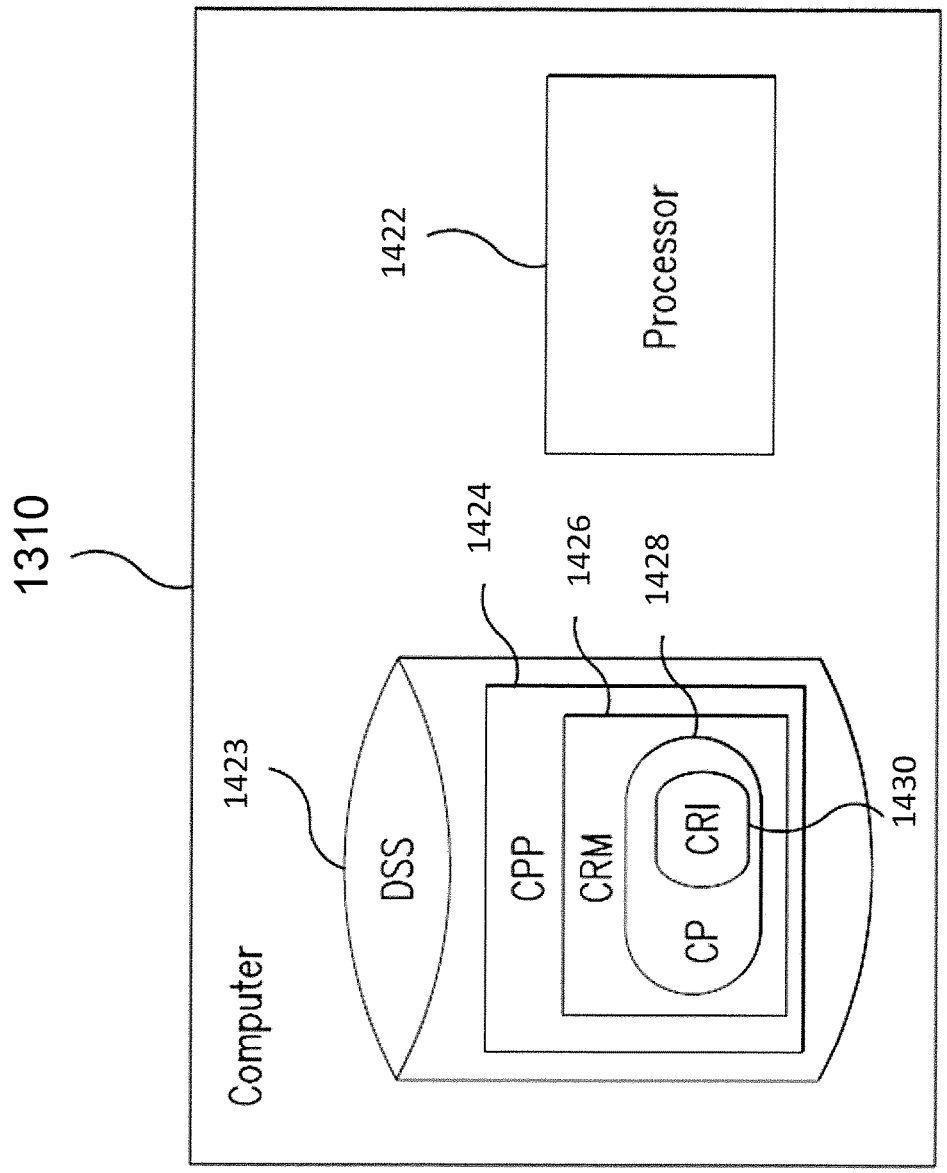
FIG. 7 illustrates a block diagram of a computer of the management system according to some embodiments.

FIG. 7 is a block diagram of a non-limiting embodiment of the computer 1310 of the management system 111. As shown in FIG. 7, the computer 1310 may include one or more processors 1422 (e.g., a general purpose microprocessor) and/or one or more circuits, such as an application specific integrated circuit (ASIC), field-programmable gate arrays (FPGAs), a logic circuit, and the like. In some embodiments, the computer 1310 may include a data storage system (DSS) 1423. The DSS 1423 may include one or more non-volatile storage devices and/or one or more volatile storage devices (e.g., random access memory (RAM)). In some embodiments where the computer 1310 includes a processor 1422, the DSS 1423 may include a computer program product (CPP) 1424. CPP 1424 may include or be a computer readable medium (CRM) 1426. The CRM 1426 may store a computer program (CP) 1428 comprising computer readable instructions (CRI) 1430. CRM 1426 may be a non-transitory computer readable medium, such as, but not limited to, magnetic media (e.g., a hard disk), optical media (e.g., a DVD), solid state devices (e.g., random access memory (RAM) or flash memory), and the like. In some embodiments, the CRI 1430 of computer program 1428 may be configured such that when executed by processor 1422, the CRI 1430 causes the computer 1310 to perform steps described above (e.g., steps described above with reference to the flow charts shown in FIGS. 4 and 5). In other embodiments, the computer 1310 may be configured to perform steps described herein without the need for a computer program. That is, for example, the computer 1310 may consist merely of one or more ASICs. Hence, the features of the embodiments described herein may be implemented in hardware and/or software.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

The invention claimed is:

1. An analyte monitoring system comprising:
an analyte sensor;
a transceiver configured to receive sensor data from the analyte sensor and calculate analyte monitoring information, wherein the analyte monitoring information includes one or more performance diagnostics;
a display device configured to receive the analyte monitoring information from the transceiver; and
a management system configured to:
receive analyte monitoring information from the display device;
use the analyte monitoring information to produce a comparison result, wherein using the analyte monitoring information to produce the comparison result comprises comparing the one or more performance diagnostics with one or more performance indicators, and the management system calculates at least one of the one or more performance indicators using one or more of (i) sensor shipment information, (ii) insertion dates of one or more sensors, (iii) removal dates of one or more sensors, and (iv) a number of days since implant of one or more sensors; and
determine, based on the comparison result, whether a condition is satisfied; and
in response to determining that the condition is satisfied, transmit to the display device management information associated with the received analyte monitoring information.

2. The analyte monitoring system of claim 1, wherein the one or more performance indicators include one or more performance thresholds, and comparing the analyte monitoring information with the one or more performance indicators comprises comparing the one or more performance diagnostics with the one or more performance thresholds.

3. The analyte monitoring system of claim 1, wherein the management information includes a replacement date for the sensor.

4. The analyte monitoring system of claim 1, wherein the management information includes a command that instructs the display device to transmit information to the transceiver.

5. The analyte monitoring system of claim 1, wherein the management system is further configured to generate compliance information based on the analyte monitoring information;
wherein using the analyte monitoring information to produce the comparison result comprises comparing the compliance information with usage protocol information.

6. The analyte monitoring system of claim 5, wherein the analyte monitoring information includes calibration data, the management system is configured to generate the compliance information based on the calibration data, the usage protocol information comprises one or more compliance thresholds, and comparing the compliance information with the usage protocol information comprises comparing the compliance information with the one or more compliance thresholds.

7. The analyte monitoring system of claim 5, wherein the management information includes a command for the display device to display a compliance alert.

8. The analyte monitoring system of claim 1, wherein:
the analyte monitoring information includes battery information;
using the analyte monitoring information to produce the comparison result comprises comparing the battery information with a battery threshold;
the condition is satisfied in response to determining that the battery voltage is below the battery threshold; and
the management information includes an instruction for the display device to display a battery replacement alert.

9. The analyte monitoring system of claim 1, wherein the analyte sensor is a first analyte sensor, the transceiver is a first transceiver, the display device is a first display device, the sensor data is first sensor data, the analyte monitoring information is first analyte monitoring information, the comparison result is a first comparison result, the condition is a first condition, and the analyte monitoring system further comprises:
a second analyte sensor;
a second transceiver configured to receive second sensor data from the second analyte sensor and calculate second analyte monitoring information; and
a second display device configured to receive the second analyte monitoring information from the transceiver;
wherein the management system is further configured to:
receive second analyte monitoring information from the second display device;
use the second analyte monitoring information to produce a second comparison result; and
determine, based on the second comparison result, whether a second condition is satisfied; and
in response to determining that the second condition is satisfied, transmit to the second display device management information associated with the received second analyte monitoring information.

10. The analyte monitoring system of claim 9, wherein the first analyte monitoring information includes one or more first performance diagnostics, the second analyte monitoring information includes one or more second performance diagnostics, the first and second analyte sensors are part of a sensor lot, using the first analyte monitoring information to produce the first comparison result comprises comparing the one or more first performance diagnostics with one or more sensor lot performance indicators, and using the second analyte monitoring information to produce the second comparison result comprises comparing the one or more second performance diagnostics with the one or more sensor lot performance indicators.

11. The analyte monitoring system of claim 10, wherein the management system is further configured to calculate one or more sensor lot performance diagnostics using the one or more first performance diagnostics and the one or more second performance diagnostics.

12. The analyte monitoring system of claim 11, wherein the management system is further configured to modify one or more of the one or more sensor lot performance indicators using the one or more sensor lot performance diagnostics.

13. The analyte monitoring system of claim 9, wherein the first analyte monitoring information includes one or more first performance diagnostics, the second analyte monitoring information includes one or more second performance diagnostics, the first and second transceivers are part of a transceiver lot, using the first analyte monitoring information to produce the first comparison result comprises comparing the one or more first performance diagnostics with one or more transceiver lot performance indicators, and using the second analyte monitoring information to produce the second comparison result comprises comparing the one or more second performance diagnostics with the one or more transceiver lot performance indicators.

14. The analyte monitoring system of claim 13, wherein the management system is further configured to calculate one or more transceiver lot performance diagnostics using the one or more first performance diagnostics and the one or more second performance diagnostics.

15. The analyte monitoring system of claim 14, wherein the management system is further configured to modify one or more of the one or more transceiver lot performance indicators using the one or more transceiver lot performance diagnostics.

16. A method performed in a management system of an analyte monitoring system, the method comprising:
the management system receiving analyte monitoring information from a display device in communication with a transceiver that is in communication with a sensor, wherein the analyte monitoring information includes one or more performance diagnostics;
the management system using the analyte monitoring information to produce a comparison result, wherein using the analyte monitoring information to produce the comparison result comprises comparing the one or more performance diagnostics with one or more performance indicators, and at least one of the one or more performance indicators is calculated by the management system using one or more of (i) sensor shipment information, (ii) insertion dates of one or more sensors, (iii) removal dates of one or more sensors, and (iv) a number of days since implant of one or more sensors;
the management system determining, based on the comparison result, whether a condition is satisfied; and
in response to determining that the condition is satisfied, the management system transmitting, to the display device, management information associated with the received analyte monitoring information.

17. The method of claim 16, wherein the one or more performance indicators include one or more performance thresholds, and comparing the analyte monitoring information with the one or more performance indicators comprises comparing the one or more performance diagnostics with the one or more performance thresholds.

18. The method of claim 16, wherein the management information includes a replacement date for the sensor.

19. The method of claim 16, wherein the management information includes a command that instructs the display device to transmit information to the transceiver.

20. The method of claim 16, further comprising the management system generating compliance information based on the analyte monitoring information;
wherein using the analyte monitoring information to produce the comparison result comprises comparing the compliance information with usage protocol information.

21. The method of claim 20, wherein the analyte monitoring information includes calibration data, the compliance information is generated based on the calibration data, the usage protocol information comprises one or more compliance thresholds, and comparing the compliance information with the usage protocol information comprises comparing the compliance information with the one or more compliance thresholds.

22. The method of claim 20, wherein the management information includes a command for the display device to display a compliance alert.

23. The method of claim 16, wherein:
the analyte monitoring information includes battery information,
using the analyte monitoring information to produce the comparison result comprises comparing the battery information with a battery threshold,
the condition is satisfied in response to determining that the battery information is below the battery threshold, and
the management information includes an instruction for the display device to display a battery replacement alert.

24. The method of claim 16, wherein the at least one calculated performance indicator provides a variation between sensor to sensor lots or transmitter to transmitter lots.

25. The method of claim 16, wherein the sensor is a first sensor, the transceiver is a first transceiver, the display device is a first display device, the analyte monitoring information is first analyte monitoring information, the comparison result is a first comparison result, the condition is a first condition, and the method further comprises:
the management system receiving second analyte monitoring information from a second display device in communication with a second transceiver that is in communication with a second sensor;
the management system using the second analyte monitoring information to produce a second comparison result;
the management system determining, based on the second comparison result, whether a second condition is satisfied; and
in response to determining that the second condition is satisfied, the management system transmitting, to the second display device, second management information associated with the received second analyte monitoring information.

26. The method of claim 25, wherein the first analyte monitoring information includes one or more first performance diagnostics, the second analyte monitoring information includes one or more second performance diagnostics, the first and second sensors are part of a sensor lot, using the first analyte monitoring information to produce the first comparison result comprises comparing the one or more first performance diagnostics with one or more sensor lot performance indicators, and using the second analyte monitoring information to produce the second comparison result comprises comparing the one or more second performance diagnostics with the one or more sensor lot performance indicators.

27. The method of claim 26, further comprising the management system calculating one or more sensor lot performance diagnostics using the one or more first performance diagnostics and the one or more second performance diagnostics.

28. The method of claim 27, further comprising the management system modifying one or more of the one or more sensor lot performance indicators using the one or more sensor lot performance diagnostics.

29. The method of claim 16, wherein the first analyte monitoring information includes one or more first performance diagnostics, the second analyte monitoring information includes one or more second performance diagnostics, the first and second transceivers are part of a transceiver lot, using the first analyte monitoring information to produce the first comparison result comprises comparing the one or more first performance diagnostics with one or more transceiver lot performance indicators, and using the second analyte monitoring information to produce the second comparison result comprises comparing the one or more second performance diagnostics with the one or more transceiver lot performance indicators.

30. The method of claim 29, further comprising the management system calculating one or more transceiver lot performance diagnostics using the one or more first performance diagnostics and the one or more second performance diagnostics.

31. The method of claim 30, further comprising the management system modifying one or more of the one or more transceiver lot performance indicators using the one or more transceiver lot performance diagnostics.

\* \* \* \* \*